United States Patent [19]

Navarrini et al.

[11] Patent Number: 5,245,054
[45] Date of Patent: Sep. 14, 1993

[54] PROCESS FOR THE DEHALOGENATION OF 1,3-DIOXOLANES

[75] Inventors: Walter Navarrini, Milan; Letanzio Bragante, Padova, both of Italy

[73] Assignee: Spherilene S.r.l., Milan, Italy

[21] Appl. No.: 831,162

[22] Filed: Feb. 5, 1992

[30] Foreign Application Priority Data

Feb. 7, 1991 [IT] Italy .................. MI 91 A 000319

[51] Int. Cl.⁵ .................................. C07D 317/42
[52] U.S. Cl. ................................................ 549/455
[58] Field of Search ...................................... 549/455

[56] References Cited

U.S. PATENT DOCUMENTS

| | | | |
|---|---|---|---|
| 3,865,845 | 2/1975 | Resnick | 549/455 |
| 4,393,227 | 7/1983 | Squire | 549/455 |
| 4,485,250 | 9/1982 | Squire | 549/455 |
| 4,496,750 | 1/1985 | Anderson et al. | 549/455 |
| 4,533,741 | 8/1985 | Squire | 549/455 |
| 4,535,175 | 8/1985 | Squire | 549/455 |
| 4,908,461 | 3/1990 | Hung | 549/455 |

Primary Examiner—Nicky Chan
Attorney, Agent, or Firm—Bryan Cave

[57] ABSTRACT

A process for the dehalogenation of 1,3-dioxolanes of formula:

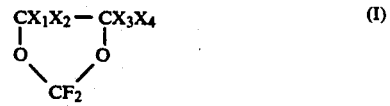

wherein $X_1$ and $X_3$, like or different from each other, are Cl or Br, $X_2$ and $X_4$, like or different from each other, are F or H. Said process consists in contacting the dioxolane of formula (I) with metallic zinc at a temperature ranging from $+30°$ to $130°$ C. The corresponding dioxoles are obtained.

4 Claims, No Drawings

PROCESS FOR THE DEHALOGENATION OF 1,3-DIOXOLANES

The present invention relates to a process for the dehalogenation of 1,3-dioxolanes to obtain the corresponding dioxoles.

More in particular, the present invention relates to a process for dehalogenating halogenated 1,3-dioxolanes of formula:

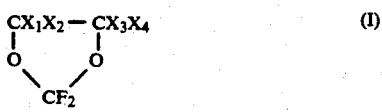

wherein: $X_1$ and $X_3$, like or different from each other, are Cl or Br, $X_2$ and $X_4$, like or different from each other, are F or H, by removal of the two vicinal halogens $X_1$ and $X_3$, and the consequent obtainment of the dioxoles of formula:

wherein: $X_2$ and $X_4$ are the same as defined hereinbefore.

The growing demand for the abovesaid fluorodioxoles, for the use thereof as monomers in the preparation of fluoropolymers, justifies the interest in perfecting the processes for the dehalogenation of the corresponding dioxolanes.

In fact, as is apparent from the prior art, the dehalogenation reactions of 1,3-dioxolanes are affected by problems concerning both reproducibility and yield.

U.S. Pat. Nos. 3,865,845 and 3,978,030 describe a process for dehalogenating fluorinated dioxolanes in an organic solvent in the presence of magnesium. However, the yields of this reaction are low and not reproducible. There is also described the debromination reaction, with metal zinc, of perfluoro-2,2-dimethyl-4,5-dibromo-1,3-dioxolane, prepared by treating perfluoro-2,2-dimethyl-1,3-dioxole with bromine. There is obtained the starting dioxole with low yields.

U.S. Pat. No. 4,393,227 describes an improved dechlorination process with magnesium, a mercury salt or metallic mercury, iodine and tetrahydrofuran, by means of which process the reproducibility of the yields is improved. The drawback of this process, however, resides in that the molar ratios among the metals shall be exact and defined, since even slight variations result in a drastic reduction of the dioxol yield.

Using this type of magnesium-based reagent, in U.S. Pat. Nos. 4,485,250 and 4,499,264 perfluoro-1,3-dioxole was prepared starting from the corresponding 4,5-dichlorodioxolane.

In U.S. Pat. No. 4,535,175 2,2-bis(trifluoromethyl)-4,4,5-trichloro-5-fluoro-1,3-dioxolane is dechlorinated either with metal zinc and zinc chloride, or with magnesium, mercury chloride, iodine and tetrahydrofuran. The dioxole yield is much higher when the magnesium-based reagent is utilized.

Analogously, in U.S. Pat. No. 4,810,806 2-trifluoromethyl-2-cyanodifluoromethyl-4,4,5-trichloro-5-fluoro-1,3-dioxolane is dechlorinated in the presence of zinc, providing low dioxole yields. The corresponding dioxolane, in which a Cl in position 4 is substituted by a F, is dechlorinated with the magnesium-based reagent; only very low amounts of the desired dioxole are obtained.

Lastly, in U.S. Pat. No. 4,908,461 there are used $LiAlH_4$ and $TiCl_3$ or $TiCl_4$ in tetrahydrofuran in particular molar ratios and according to a quite complex methodology.

From the examination of the prior art it is therefore apparent that in order to dechlorinate 2,2-difluoro-1,3-dioxolanes it was necessary to operate according to complicated methodologies in the presence of complex and not easily utilizable reagents, not always obtaining, however, high and constant yields.

Thus, it is object of the present invention to provide a perfected process for the dehalogenation of 2,2-difluoro-1,3-dioxolanes, which is easy to carry into effect, utilizes simple reagents and provides high and constant yields.

This object is achieved, according to the invention, by a process for the dehalogenation of 1,3-dioxolanes of formula:

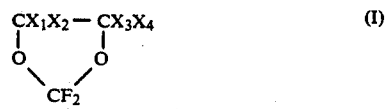

wherein: $X_1$ and $X_3$, like or different from each other, are Cl or Br, $X_2$ and $X_4$, like or different from each other, are F or H, characterized in that the dioxolane of formula (I) is brought into contact with metallic zinc in an at least stoichiometric amount and that, on conclusion of the reaction, the dioxole of formula:

wherein $X_2$ and $X_4$ are the same as defined hereinbefore, is isolated.

The reaction temperature usually ranges from $+30°$ to $+130°$ C.; preferably it ranges from $+50°$ to $+100°$ C.

The dioxolanes of formula (I) are preparable according to the methods described in the prior art, for example in U.S. Pat. Nos. 3,865,845 and 4,485,250 and in Italian patent application 20578/A 90 in the name of the Applicant.

Among the utilized dioxolanes there are preferred the ones in which $X_2$ and $X_4$ are F. Particularly preferred are 4,5-dichloro-tetrafluoro-1,3-dioxolane and 4,5-dibromo-tetrafluoro-1,3-dioxolane. Starting from these reagents, perfluoro-1,3-dioxole is obtained from the dehalogenation reaction.

The zinc/dioxolane molar ratio can vary over a relatively wide range. Generally it is higher than 1, preferably it ranges from 1.5 to 3.0.

In a preferred embodiment of the invention, the starting dioxolane is fed to the reaction vessel maintained at the reaction temperature, said reaction vessel containing the metallic zinc along with an optional solvent and, preferably, little amounts of sodium or potassium iodide and of sodium or potassium carbonate.

On conclusion of the reaction, the reaction products are collected in a trap maintained at a lower temperature than the boiling temperature of said products.

To favour this operation it is preferable to provide a nitrogen gas flow in the reaction vessel.

If a solvent is utilized, it must be inert under the reaction conditions, and preferably it is selected from amides (such as dimethylformamide), ethers (such as dioxane) and sulphoxides (such as dimethylsulphoxide).

Usually it is operated at about atmospheric pressure. However it is possible to use both reduced pressures and pressures higher than 1 atmosphere.

The reaction time is not a critical parameter; usually, the reaction is complete in a few minutes.

The resulting dioxoles can be utilized as monomers for preparing copolymers and homopolymers as is described for example in published European application No. 80,187 and U.S. Pat. Nos. 4,535,175 and 3,978,030.

The abovesaid polymers are used, besides, as anticorrosive coating material or as sheaths for optical fibers.

For a better understanding of the possible embodiments of the present invention, a few illustrative but not limitative examples are given hereinafter.

EXAMPLE 1

Dehalogenation of 4,5-dichloro-tetrafluoro-1,3-dioxolane

Operating in a nitrogen atmosphere, Zn (4.4 g), KI (180 mg), $K_2CO_3$ (300 mg) and dimethylformamide (DMF) (7 ml) were introduced into a 50 ml flask equipped with thermometer, dropping funnel, distillation column and magnetic stirrer.

Then, after having brought the mixture to 60° C., 2.75 g of 4,5-dichloro-tetrafluoro-1,3-dioxolane (synthesized according to the method described in Italian application No. 20578/A 90) dissolved in 2.5 ml of DMF were very slowly dropped in one hour into said mixture. During dropping, the mixture was heated up to 100° C. and perfluoro-1,3-dioxol was distilled off as it formed.

In the collecting flask there were condensed 1.76 g of distillate, which, subjected to gas chromatographic analysis is (column sp 1000, from 50° C. to 180° C., 10° C./min.), resulted to be composed of perfluoro-1,3-dioxole (82.2%), 4-chloro-2,2,4,5-tetrafluoro-1,3-dioxolane (3%) and 4,5-dichloro-2,2,4,5-tetrafluoro-1,3-dioxolane (15%).

The mixture was then distilled in a conventional vacuum line through four traps cooled to −80° C., −130° C., −150° C. and −196° C.

1.370 g of perfluoro-1,3-dioxole were collected in the trap cooled to −150° C.

The isolated perfluoro-1,3-dioxol yield, calculated on the converted product, was equal to 82%.

EXAMPLE 2

Dehalogenation of 4,5-dibromo-tetrafluoro-1,3-dioxolane

Into a three-neck flask equipped with reflux cooler, an inlet for a slight carrying nitrogen flow, and a rubber bottom, there were charged 2 ml of previously anhydrified dimethylformamide, 0.53 g of previously activated zinc powder, 0.05 g of KI, 0.07 g of $K_2CO_3$. The zinc powder had been previously washed with diluted hydrochloric acid, then with water and methanol and lastly it was dried under vacuum.

The reflux cooler, the top of which had been connected with a collecting trap maintained at −78° C., was cooled to 0° C. and the reaction flask was maintained at +60° C.

Then, with the reaction mixture being maintained under stirring, through the bottom there were injected 0.53 g (1.71 mmols) of 4,5-dibromo-tetrafluoro-1,3-dioxolane, synthesized by adding bromine to perfluoro-1,3-dioxole. The reaction was concluded in a few minutes and in the trap at −78° C. there were collected 1.48 mmols of liquid tetrafluoro-1,3-dioxole; its $^{19}$F-NMR and IR spectra were corresponding to the ones of an authentic sample.

The yield of this reaction was 86%.

EXAMPLE 3 (COMPARATIVE TEST)

Dehalogenation of perfluoro-2,2-dimethyl-4,5-dibromo-1,3-dioxolane

Operating in like manner as in example 2, 0.69 g (1.7 mmols) of perfluoro-2,2-dimethyl-4,5-dibromo-1,4-dioxolane, synthesized by adding bromine to perfluoro-2,2-dimethyl-1,3-dioxole, were charged into the reaction vessel.

0.25 mmols of perfluoro-2,2-dimethyl-1,3-dioxole were collected.

The reaction yield was equal to 15%.

We claim:

1. A process for the dehalogenation of 1,3-dioxolanes of the formula:

wherein:

$X_1$ and $X_3$, like or different from each other, are Cl or Br, characterized in that the compound of formula (I) is brought into contact with metallic zinc in an at least stoichiometric amount, in the presence of an amide, at a temperature ranging from +30° to +130° C., and that, on conclusion of the reaction, the dioxole of the formula:

is separated.

2. The process of claim 1, wherein the amide is dimethylformamide.

3. The process of claim 1, wherein the reaction is conducted at a temperature ranging from +50° to +100° C.

4. The process of claim 1, wherein the reaction is conducted in the presence of sodium or potassium iodide and of sodium or potassium carbonate.

* * * * *

UNITED STATES PATENT AND TRADEMARK OFFICE
CERTIFICATE OF CORRECTION

PATENT NO.   : 5,245,054
DATED        : September 14, 1993
INVENTOR(S)  : Walter Navarini, et al It is certified that error appears in the above-indentified patent and that said Letters Patent is hereby corrected as shown below:

On the title page, item [73] Assignee: should read --Ausimont S.p.a., Milan, Italy--.

Signed and Sealed this

Sixth Day of June, 1995

BRUCE LEHMAN

*Attest:*

*Attesting Officer*            *Commissioner of Patents and Trademarks*